United States Patent
Zhang et al.

(10) Patent No.: US 11,304,945 B2
(45) Date of Patent: Apr. 19, 2022

(54) PHARMACEUTICAL COMPOSITION AND METHOD FOR PREPARING SAME

(71) Applicant: Jiangsu Hengrui Medicine Co., Ltd., Jiangsu (CN)

(72) Inventors: Daimei Zhang, Jiangsu (CN); Tingting Zhang, Jiangsu (CN); Huan Ding, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 109 days.

(21) Appl. No.: 16/626,910

(22) PCT Filed: Jul. 3, 2018

(86) PCT No.: PCT/CN2018/094211
§ 371 (c)(1),
(2) Date: Dec. 27, 2019

(87) PCT Pub. No.: WO2019/007317
PCT Pub. Date: Jan. 10, 2019

(65) Prior Publication Data
US 2020/0171031 A1    Jun. 4, 2020

(30) Foreign Application Priority Data

Jul. 4, 2017 (CN) .......................... 201710536705.9
Nov. 10, 2017 (CN) .......................... 201711105075.6

(51) Int. Cl.
*A61K 31/5025* (2006.01)
*A61K 9/10* (2006.01)
*A61K 47/38* (2006.01)

(52) U.S. Cl.
CPC ............ *A61K 31/5025* (2013.01); *A61K 9/10* (2013.01); *A61K 47/38* (2013.01)

(58) Field of Classification Search
CPC .................................................. A61K 31/5025
See application file for complete search history.

(56) References Cited

FOREIGN PATENT DOCUMENTS

| | | |
|---|---|---|
| CN | 105899212 A | 8/2016 |
| CN | 106573001 A | 4/2017 |
| CN | 106573002 A | 4/2017 |
| WO | 2013184572 A1 | 12/2013 |
| WO | 2016007185 A1 | 1/2016 |
| WO | 2016145138 A1 | 9/2016 |

OTHER PUBLICATIONS

The second method (paddle method) of the dissolution rate test described in general rule 0931 of vol. IV of Chinese Pharmacopoeia 2015 Edition.
Extended European Search Report dated Mar. 25, 2021 in corresponding EP No. 18828577.9.

*Primary Examiner* — Paul V Ward
(74) *Attorney, Agent, or Firm* — Ice Miller LLP

(57) ABSTRACT

A solid dispersion, a method for preparing same, and a solid preparation including the solid dispersion. The solid dispersion contains (R)-4-amino-1-(1-(but-2-ynylacyl)pyrrolidin-3-yl)-3-(4-(2,6-difluorophenoxy)phenyl)-1,6-dihydro-7H-pyrrolo[2,3-d]pyridazine-7-one or a pharmaceutically acceptable salt thereof, and a carrier material. The carrier material is selected from hydroxypropyl methylcellulose acetate succinate and hydroxypropyl methylcellulose phthalate.

16 Claims, 4 Drawing Sheets

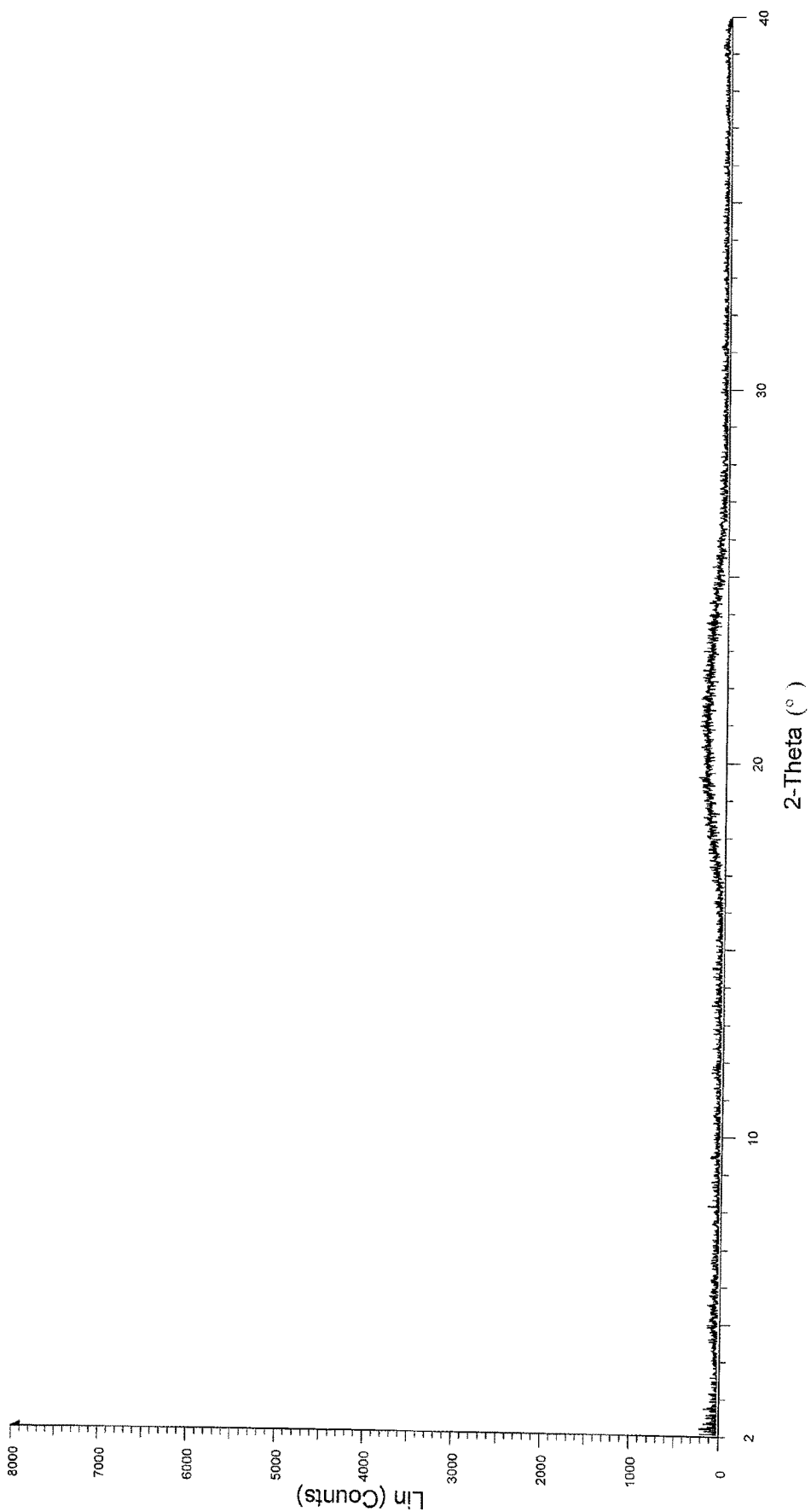

PHARMACEUTICAL COMPOSITION AND METHOD FOR PREPARING SAME

CROSS-REFERENCE TO RELATED APPLICATION

This application is a Section 371 of International Application No. PCT/CN2018/094211, filed Jul. 3, 2018, which was published in the Chinese language on Jan. 1, 2019, under International Publication No. WO 2019/007317 A1, which claims priority under 35 U.S.C. § 119(b) to Chinese Application No. 201710536705.9, filed Jul. 4, 2017, and to Chinese Application No. 201711105075.6, filed Nov. 10, 2017, the disclosures of all of which are incorporated herein by reference in their entirety.

FIELD OF THE INVENTION

The present disclosure belongs to the field of pharmaceutical formulations, and specifically relates to a solid dispersion comprising (R)-4-amino-1-(1-(but-2-ynoyl)pyrrolidin-3-yl)-3-(4-(2,6-difluorophenoxy)phenyl)-1,6-dihydro-7H-pyrrolo[2,3-d]pyridazin-7-one and a method for preparing the same.

BACKGROUND OF THE INVENTION

B cell lymphoma is one of the common malignant tumors affecting human health, and accounts for 70-80% of malignant lymphoma. The incidence rate of B cell lymphoma is increasing year by year. It is one of the common malignant tumors in China. The occurrence of B cell lymphoma is affected by a variety of factors including genetic factors, biological factors, and physical and chemical factors. B cell lymphoma has a poor prognosis, and the survival is still low under current treatment regimens.

Rheumatoid arthritis (RA) is a chronic autoimmune disease that mainly affects facet joints. The pathological features of rheumatoid arthritis are mainly the infiltration of inflammatory cells, the hyperplasia and hypertrophy of synovial tissue, as well as bone damage. Its etiology and pathogenesis have not been fully elucidated. The incidence of rheumatoid arthritis is high, being about 0.5 to 1% in adults.

In B cell lymphoma, inhibition of BTK activity is effective in inhibiting tumor cell proliferation and survival. The representative drug, ibrutinib, has been approved by the U.S. FDA for treating mantle cell lymphoma and chronic lymphocytic leukemia, and has clinically shown an excellent efficacy.

In rheumatoid arthritis, inhibition of BTK activity can inhibit the activity of transcription factors such as NF-κB, thereby inhibiting the release of inflammatory factors and reducing inflammation symptoms. The BTK small molecule inhibitor HM61713 developed by Hanmi Pharmaceuticals preclinically shows an excellent anti-arthritic effect, and is currently undergoing phase I clinical trial.

WO2013184572 discloses an oral formulation of ibrutinib, comprising ibrutinib, a diluent, a disintegrant, a surfactant and a lubricant, to meet the requirements of dissolution, stability and bioavailability for preparing ibrutinib drug.

WO2016007185 discloses a compound of formula I, namely (R)-4-amino-1-(1-(but-2-ynoyl)pyrrolidin-3-yl)-3-(4-(2,6-difluorophenoxy)phenyl)-1,6-dihydro-7H-pyrrolo[2,3-d]pyridazin-7-one, which is structurally similar to ibrutinib. The compound of formula I has features such as good target specificity, high selectivity to kinase, and high oral bioavailability. It is expected to reduce or eliminate the clinically adverse reaction of ibrutinib, and will exert therapeutic advantages in areas such as B cell lymphoma and rheumatoid arthritis.

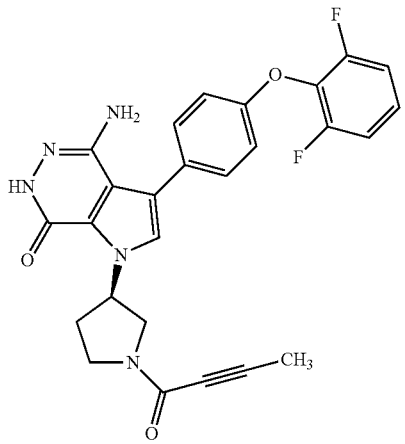

There are a number of challenges for pharmaceutical active compounds with low solubility during the preparation of high-quality pharmaceutical compositions or formulations such as tablets, granules and powder. Researchers need to investigate and solve the problems encountered.

SUMMARY OF THE INVENTION

In one aspect of the present disclosure, the active ingredient (R)-4-amino-1-(1-(but-2-ynoyl)pyrrolidin-3-yl)-3-(4-(2,6-difluorophenoxy)phenyl)-1,6-dihydro-7H-pyrrolo[2,3-d]pyridazin-7-one or a pharmaceutically acceptable salt thereof is dispersed in the structure of a drug-loading material by a solvent with a solid dispersion technique to form a co-dispersion system of drug and carrier material, thereby solving the problem of its poor solubility.

The present disclosure also provides a solid dispersion of (R)-4-amino-1-(1-(but-2-ynoyl)pyrrolidin-3-yl)-3-(4-(2,6-difluorophenoxy)phenyl)-1,6-dihydro-7H-pyrrolo[2,3-d]pyridazin-7-one or a pharmaceutically acceptable salt thereof, comprising (R)-4-amino-1-(1-(but-2-ynoyl)pyrrolidin-3-yl)-3-(4-(2,6-difluorophenoxy)phenyl)-1,6-dihydro-7H-pyrrolo[2,3-d]pyridazin-7-one or a pharmaceutically acceptable salt thereof as an active ingredient, and a carrier material, wherein the carrier material is selected from the group consisting of hydroxypropyl methylcellulose acetate succinate and hydroxypropyl methylcellulose phthalate.

In some embodiments, when the weight ratio of the carrier material to the active ingredient used in the solid dispersion of the present disclosure is at least 0.5:1 or more, a uniform dispersion system of the active ingredient and the carrier can be obtained by the preparation method described herein, the crystal state of the active ingredient is changed to become amorphous, the solubility and absorption of the drug are improved, and the drug exhibits a rapid onset and high bioavailability after oral administration. The solid dispersion itself is stable, and does not appear to undergo aging or degradation for at least 6 months, and there is no significant change in various evaluation indexes.

In the solid dispersion of the present disclosure, the weight ratio of the carrier material to the active ingredient or a pharmaceutically acceptable salt thereof can vary widely, with a minimum of 0.5:1. In the present disclosure, the higher the carrier material content, the easier it is to change the active ingredient from crystalline form to an amorphous form, and the higher the corresponding bioavailability of the solid dispersion. Considering the balance between drug loading and bioavailability, the weight ratio of the carrier material to the active ingredient or a pharmaceutically acceptable salt thereof in the present disclosure can be 0.5:1 to 4:1. In some embodiments, the weight ratio can be 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.2:1, 2.4:1, 2.6:1, 2.8:1, 3:1, 3.2:1, 3.4:1, 3.6:1, 3.8:1 and 4:1, preferably 0.8:1 to 3:1, and more preferably 1:1 to 2:1.

In some embodiments, the solid dispersion of the present disclosure consists of the active ingredient (R)-4-amino-1-(1-(but-2-ynoyl)pyrrolidin-3-yl)-3-(4-(2,6-difluorophenoxy)phenyl)-1,6-dihydro-7H-pyrrolo[2,3-d]pyridazin-7-one or a pharmaceutically acceptable salt thereof and a carrier material, wherein the carrier material is selected from the group consisting of hydroxypropyl methylcellulose acetate succinate and hydroxypropyl methylcellulose phthalate.

The solid dispersion of the present disclosure can be obtained by widely known preparation methods such as melting methods, solvent methods, and solvent-melting methods. Other preparation methods include obtaining a eutectic mixture by grinding method through co-dissolution principle, and obtaining a solid surface adsorbate by dissolving the drug in an organic solvent to be dispersed and adsorbed on an inert material.

The solvent method of the present disclosure includes a coprecipitation method, wherein the drug and the carrier are dissolved together in an organic solvent, or the drug and the carrier are dissolved respectively in a solvent followed by mixing them well, or the carrier material is suspended and dispersed in an organic solvent of the active ingredient or a pharmaceutically acceptable salt thereof, and then the solvent is removed to obtain a solid dispersion. The method of removing solvent is known or determinable by those skilled in the art, and can be a method of dropwise adding a high polar organic solution to a low polar solvent to precipitate a solid, as well as a method of spray drying or drying under reduced pressure.

In one aspect of the melting method of the present disclosure, the drug and carrier are mixed well and heated to melt, or the carrier is heated to melt followed by adding the drug to dissolve by stirring, and then the melt is rapidly cooled to a solid under vigorous stirring, or directly poured into a capsule and then cooled.

In one aspect of the solvent-melting method of the present disclosure, the drug is dissolved in a small amount of organic solvent, mixed well with the melted carrier, evaporated to remove the organic solvent, and cooled to obtain a solid.

The method for preparing the solid dispersion of the present disclosure is preferably a solvent method (also known as coprecipitation method), comprising the steps of dissolving the carrier material and the active ingredient or a pharmaceutically acceptable salt thereof together in an organic solvent, or suspending and dispersing the carrier material in an organic solvent of the active ingredient or a pharmaceutically acceptable salt thereof, and then removing the organic solvent to obtain the solid dispersion.

Furthermore, the method of removing organic solvent is known or determinable by those skilled in the art, and can be a method of dropwise adding a high polar organic solution to a low polar solvent or water to precipitate a solid (namely solvent-precipitating method), as well as a method of spray drying or drying under reduced pressure.

In some embodiments, the solid dispersion of the present disclosure is obtained by dissolving the active ingredient or a pharmaceutically acceptable salt thereof and the carrier material hydroxypropyl methylcellulose acetate succinate together in a first organic solvent, and then adding dropwise the resulting solution to a second solvent. The dropwise addition rate is preferably 1 to 100 g/min, more preferably 2 to 50 g/min, and specifically 2, 6, 10, 14, 16, 20, 24, 28, 32, 36, 40, 44, 48 or 50 g/min. Furthermore, the above method for preparing the composition can comprise any one step of filtration, washing and drying, in order to ensure that the amount of residual solvent in the resulting solid dispersion is less than 120 ppm in order to meet the requirements for preparing the solid dispersion into a drug.

Furthermore, the first solvent can be a high polar organic solvent that is known or determinable by those skilled in the art, and includes, but is not limited to, a sulfone solvent such as dimethyl sulfoxide, an amide solvent such as N,N-dimethylformamide and N,N-dimethylacetamide, a ketone solvent such as acetone, a halogenated hydrocarbon solvent such as tetrachloromethane, an alcohol solvent such as ethanol and methanol, and preferably at least one of dimethyl sulfoxide, N,N-dimethylformamide, N,N-dimethylacetamide, ethanol and methanol.

The second solvent can be a less polar solvent (also known as low polar solvent, which is miscible with the first solvent, and after being miscible with the first organic solvent, the solubility of the active ingredient or a pharmaceutically acceptable salt thereof in the system is reduced), and includes, but is not limited to, an alkane solvent such as n-hexane and petroleum ether, an alcohol solvent such as ethanol and methanol, a furan solvent such as tetrahydrofuran, an ether solvent such as diethyl ether and dipropyl ether, and water or an acidic aqueous solution, and preferably at least one of methanol, ethanol, water and an acidic aqueous solution.

In an embodiment, the active ingredient or a pharmaceutically acceptable salt thereof and the carrier material are dissolved together in at least one organic solvent selected from the group consisting of dimethyl sulfoxide, N,N-dimethylformamide and N,N-dimethylacetamide, and then the resulting solution is added dropwise to water. The dropwise addition rate is preferably 1 to 100 g/min, more preferably 2 to 50 g/min, and specifically 2, 6, 10, 14, 16, 20, 24, 28, 32, 36, 40, 44, 48 or 50 g/min.

The solid dispersion of the present disclosure can be further formulated into a solid formulation such as a tablet, pill, granule, capsule and the like. The amount of the active ingredient or a pharmaceutically acceptable salt thereof is 8 to 40%, and can be 8, 9, 10, 11, 12, 13, 14, 15, 16, 17, 18, 19, 20, 21, 22, 23, 24, 25, 26, 27, 28, 29, 30, 35 or 40%, and preferably 15 to 25% by weight of the solid formulation.

In some embodiments, the amount (weight or mass) of the active ingredient or a pharmaceutically acceptable salt thereof of the present disclosure is 10 to 500 mg, and can be 200 mg, 190 mg, 180 mg, 170 mg, 160 mg, 150 mg, 140 mg, 130 mg, 120 mg, 110 mg, 100 mg, 95 mg, 75 mg, 50 mg, 25 mg, 15 mg and 10 mg, and preferably 200 mg, 100 mg or 25 mg. Furthermore, the solid formulation also comprises a pharmaceutically acceptable excipient that is well known or determinable by those skilled in the art, and includes, but is not limited to, at least one of a disintegrant, filler, binder and lubricant.

In some embodiments, in a medium, 0.15% aqueous solution of sodium dodecyl sulfate (SDS), the dissolution rate (%) of the active ingredient in the solid formulation of the present disclosure is 85% or more, and can be greater than or equal to 85, 86, 87, 88, 89, 90, 91, 92, 93, 94, 95, 96, 97, 98, 99 and 100%, and preferably 90% or more in 45 min; furthermore, the dissolution rate (%) of the active ingredient in the solid formulation is 70% or more, and can be greater than or equal to 70, 71, 72, 73, 74, 75, 76, 77, 78, 79, 80, 81, 82, 83, 84, 85, 86, 87, 88, 89, 90, 91, 92, 93, 94 and 95% in 15 min. The solid formulation dissolves rapidly and completely, and has a good bioavailability. The preparation process of the solid formulation is simple, and suitable for large-scale production.

In some embodiments, the solid formulation of the present disclosure is stable for at least 3 months, at least 6 months, at least 9 months, at least 12 months, at least 18 months or at least 24 months at 25° C./60% RH. In some embodiments, the pharmaceutical composition is stable for at least 1 month, at least 2 months, at least 3 months, or even 6 months or longer at 40° C./75% RH.

In some embodiments, the solid dispersion of the present disclosure is stable for at least 3 months, at least 6 months, at least 9 months, at least 12 months, at least 18 months or at least 24 months at 25° C./60% RH. In some embodiments, the pharmaceutical composition is stable for at least 1 month, at least 2 months, at least 3 months, or even 6 months or longer at 40° C./75% RH.

The filler provides volume to make a tablet into a practical size that can be processed. The filler can also contribute to the process, and improve the physical properties of the solid formulation such as fluidity, compressibility and hardness of solid formulation. The filler of the present disclosure is known or determinable by those skilled in the art and includes, but is not limited to, at least one of dextrin, lactose, sucrose, calcium hydrophosphate, starch, anhydrous calcium hydrophosphate, calcium hydrophosphate, microcrystalline cellulose and mannitol. Preferably, the filler is present in an amount of 30 to 90%, and more preferably 35 to 60% by weight, relative to the weight of the solid formulation. In an embodiment, the filler can be present in an amount of 35, 38, 40, 42, 45, 47, 50, 52, 55, 58 and 60% by weight, relative to the weight of the solid formulation.

The disintegrant of the present disclosure is known or determinable by those skilled in the art and includes, but is not limited to, at least one of croscarmellose sodium, crospovidone, sodium carboxymethyl starch, starch, pregelatinized starch and alginic acid. Preferably, the disintegrant is present in an amount of 1 to 20% by weight, relative to the weight of the solid formulation. In an embodiment, the disintegrant can be present in an amount of 1.0, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 and 20%, and preferably 5 to 15% by weight, relative to the weight of the solid formulation.

The binder of the present disclosure is known or determinable by those skilled in the art and includes, but is not limited to, at least one of polyvinylpyrrolidone, starch, methylcellulose, carboxycellulose, hydroxypropylcellulose, hydroxypropylmethylcellulose and alginate, and preferably at least one of polyvinylpyrrolidone (trade name K30) and hydroxypropylcellulose. More preferably, the binder is present in an amount of 0.5 to 10% by weight, relative to the weight of the solid formulation. In an embodiment, the binder can be present in an amount of 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5 and 10% by weight, relative to the weight of the solid formulation.

The lubricant of the present disclosure is known or determinable by those skilled in the art and includes, but is not limited to, at least one of magnesium stearate, stearic acid, palmitic acid, calcium stearate, talc, carnauba wax and sodium stearyl fumarate. Preferably, the lubricant of the present disclosure is present in an amount of 0.1 to 5% by weight, relative to the weight of the solid formulation. In an embodiment, the lubricant can be present in an amount of 0.1, 0.2, 0.3, 0.4, 0.5, 0.6, 0.7, 0.8, 0.9%, 1%, 1.5%, 2%, 2.5%, 3%, 3.5%, 4%, 4.5 and 5%, and preferably 0.1 to 2% by weight, relative to the weight of the solid formulation.

In a preferred embodiment, the solid formulation of the present disclosure comprises:
1) 10 mg to 500 mg of the active ingredient or a pharmaceutically acceptable salt thereof;
2) 5 to 15% by weight of a disintegrant;
3) 30 to 90% by weight of a filler;
4) 0.5 to 10% by weight of a binder; and
5) 0.1 to 5% by weight of a lubricant.

Furthermore, the carrier material in the solid formulation is hydroxypropyl methylcellulose acetate succinate.

In one embodiment, the dissolution rate of the solid formulation of the present disclosure is determined according to the second method (paddle method) of the dissolution rate test described in general rule of volume IV of Chinese Pharmacopoeia 2015 Edition. The dissolution test of the composition of the present disclosure can be carried out using 0.15% aqueous solution of sodium dodecyl sulfate (SDS), preferably 1000 ml as a dissolution medium at 37±0.5° C., and at a paddle speed of 50 rpm.

The dissolution rate of the solid dispersion of the present disclosure can be determined according to the second method (paddle method) of the dissolution rate test described in general rule of volume IV of Chinese Pharmacopoeia 2015 Edition. The dissolution test can be carried out using 1000 ml of 0.15% aqueous solution of SDS as a dissolution medium at 37±0.5° C., and at a paddle speed of 75 rpm.

The present disclosure also provides a solid formulation comprising the active ingredient (R)-4-amino-1-(1-(but-2-ynoyl)pyrrolidin-3-yl)-3-(4-(2,6-difluorophenoxy)phenyl)-1,6-dihydro-7H-pyrrolo[2,3-d]pyridazin-7-one or a pharmaceutically acceptable salt thereof and a carrier material, wherein in a medium, 0.15% aqueous solution of sodium dodecyl sulfate (SDS), the dissolution rate (%) of the active ingredient in the solid formulation is 85% or more, and can be greater than or equal to 85, 86, 87, 88, 89, 90, 91, 92, 93, 94, 95, 96, 97, 98, 99 and 100%, and preferably 90% or more in 45 min; furthermore, the dissolution rate (%) of the active ingredient in the solid formulation is 70% or more, and can be greater than or equal to 70, 71, 72, 73, 74, 75, 76, 77, 78, 79, 80, 81, 82, 83, 84, 85, 86, 87, 88, 89, 90, 91, 92, 93, 94 and 95% in 15 min. In some embodiments, the active ingredient or a pharmaceutically acceptable salt thereof and the carrier material in the solid dispersion are in the form of a solid dispersion, wherein the carrier material is selected from the group consisting of hydroxypropyl methylcellulose acetate succinate and hydroxypropyl methylcellulose phthalate, and preferably hydroxypropyl methylcellulose acetate succinate.

In one embodiment, the method for preparing the solid formulation comprising the solid dispersion of (R)-4-amino-1-(1-(but-2-ynoyl)pyrrolidin-3-yl)-3-(4-(2,6-difluorophenoxy)phenyl)-1,6-dihydro-7H-pyrrolo[2,3-d]pyridazin-7-one of the present disclosure is as follows: the solid dispersion is pulverized, mixed well with a filler and/or disintegrant required for molding a solid formulation, added with a binder, and subjected to wet granulation or dry granulation, then the resulting granules are dried, screened by a sieve, milled, mixed well with a lubricant, and prepared into pills or granules or compressed into tablets or filled into capsules; or the solid dispersion can also be added with suitable auxiliary materials and directly filled into capsules or compressed into tablets; the resulting granules or raw tablets or capsules can be further coated as needed.

The active ingredient (R)-4-amino-1-(1-(but-2-ynoyl)pyrrolidin-3-yl)-3-(4-(2,6-difluorophenoxy)phenyl)-1,6-dihydro-7H-pyrrolo[2,3-d]pyridazin-7-one of the present disclosure can react with an acid to provide a pharmaceutically acceptable salt. The acid is known or determinable by those skilled in the art and includes, but is not limited to, hydrochloric acid, methanesulfonic acid, fumaric acid, trifluoroacetic acid and phosphoric acid.

The term "relative to the weight of the solid formulation" of the present disclosure means that the calculation of usage amount ranges of the active ingredient or other kinds of pharmaceutical auxiliary materials is based on the weight of the tablet core without a coating agent, see Example 1 for details.

Typical acceptable criteria for the stability of the present disclosure are as follows: according to HPLC test, the increase of total impurity content is usually not more than about 1%, preferably not more than 0.5%, and can be 0.01%, 0.02%, 0.03%, 0.04%, 0.05%, 0.06%, 0.07%, 0.08%, 0.09%, 0.1%, 0.2%, 0.3%, 0.4% and 0.5%; or/and the total impurity content is not more than 0.5%, and can be 0.01%, 0.02%, 0.03%, 0.04%, 0.05%, 0.06%, 0.07%, 0.08%, 0.09%, 0.1%, 0.2%, 0.3%, 0.4% and 0.5%; or/and according to the X-ray powder diffraction test analysis, the physical form of the active ingredient in the solid dispersion/solid formulation remains amorphous without aging phenomenon.

X-ray powder diffraction test of the present disclosure can be carried out on a Rigaku UltimaIV composite multi-functional X-ray diffractometer. Specific acquisition information: Cu anode (40 kV, 40 mA), Cu-K$\alpha$1 ray ($\lambda$=1.5418 Å), scan rate 20°/min, scan range (2q range): 3~45°, scan step size 0.02, slit width 0.01.

HPLC detection conditions of the present disclosure: octadecylsilane bonded silica is used as the filler (Waters Symmetry C18 colume); 0.01 mol/L potassium dihydrogen phosphate buffer solution and acetonitrile are used as the mobile phase and eluent; the detection wavelength is 210 nm.

The pharmaceutical auxiliary materials and reagents, such as hydroxypropyl methylcellulose acetate succinate, are commercially available. (R)-4-Amino-1-(1-(but-2-ynoyl) pyrrolidin-3-yl)-3-(4-(2,6-difluorophenoxy)phenyl)-1,6-dihydro-7H-pyrrolo[2,3-d]pyridazin-7-one (compound A) or a pharmaceutically acceptable salt thereof can be prepared according to the method described in Example 109 of WO2016007185.

DESCRIPTION OF THE DRAWINGS

The above and other objects and features of the present disclosure will become apparent with reference to the following drawings, which respectively represent:

FIG. 4: X-ray diffraction spectrum of the solid dispersion of Experimental Example 3.

DETAILED DESCRIPTION OF THE INVENTION

Figure 1:
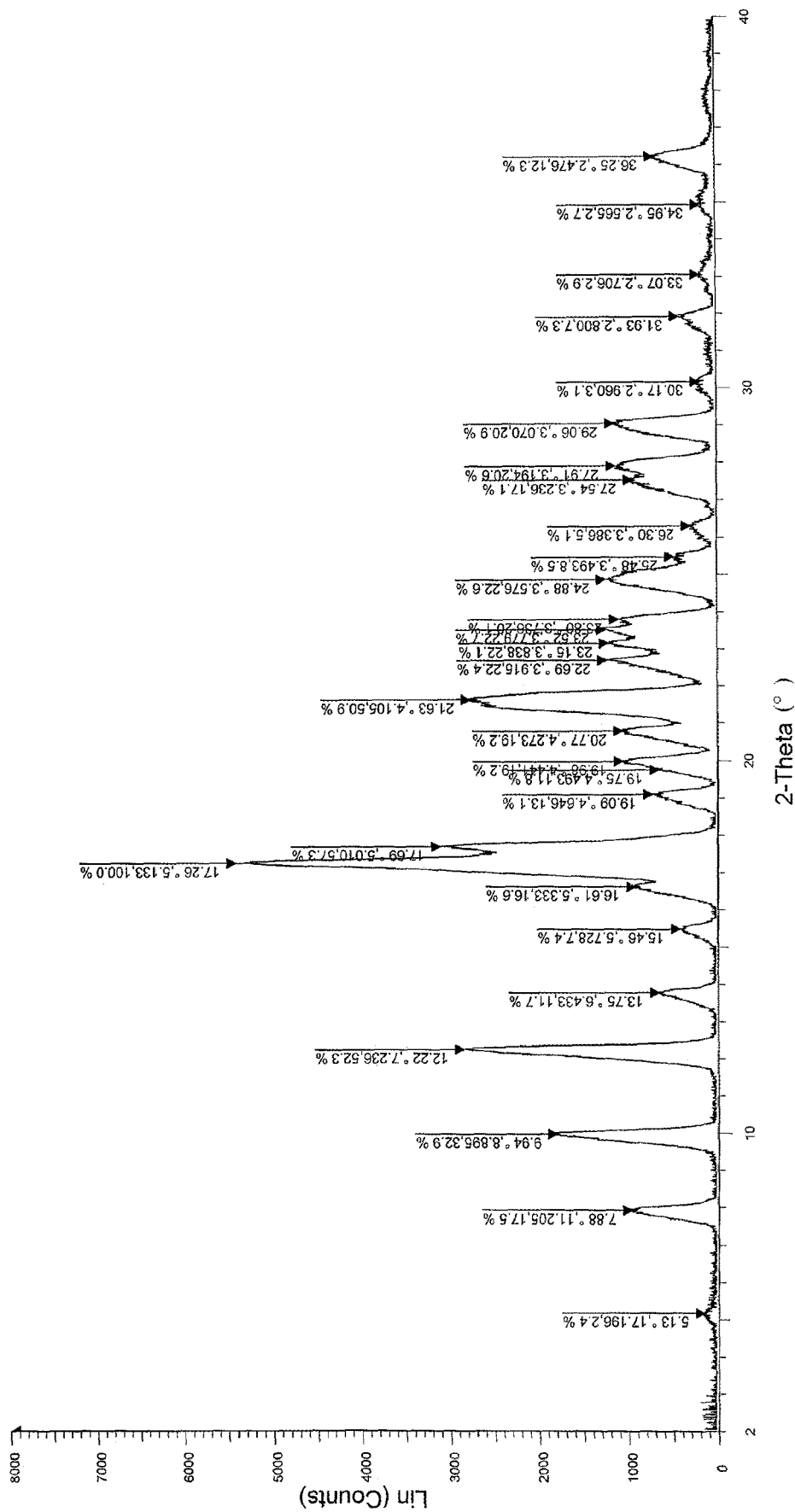
FIG. 1: X-ray diffraction spectrum of the Active Pharmaceutical Ingredient (API) compound A.
Figure 2:
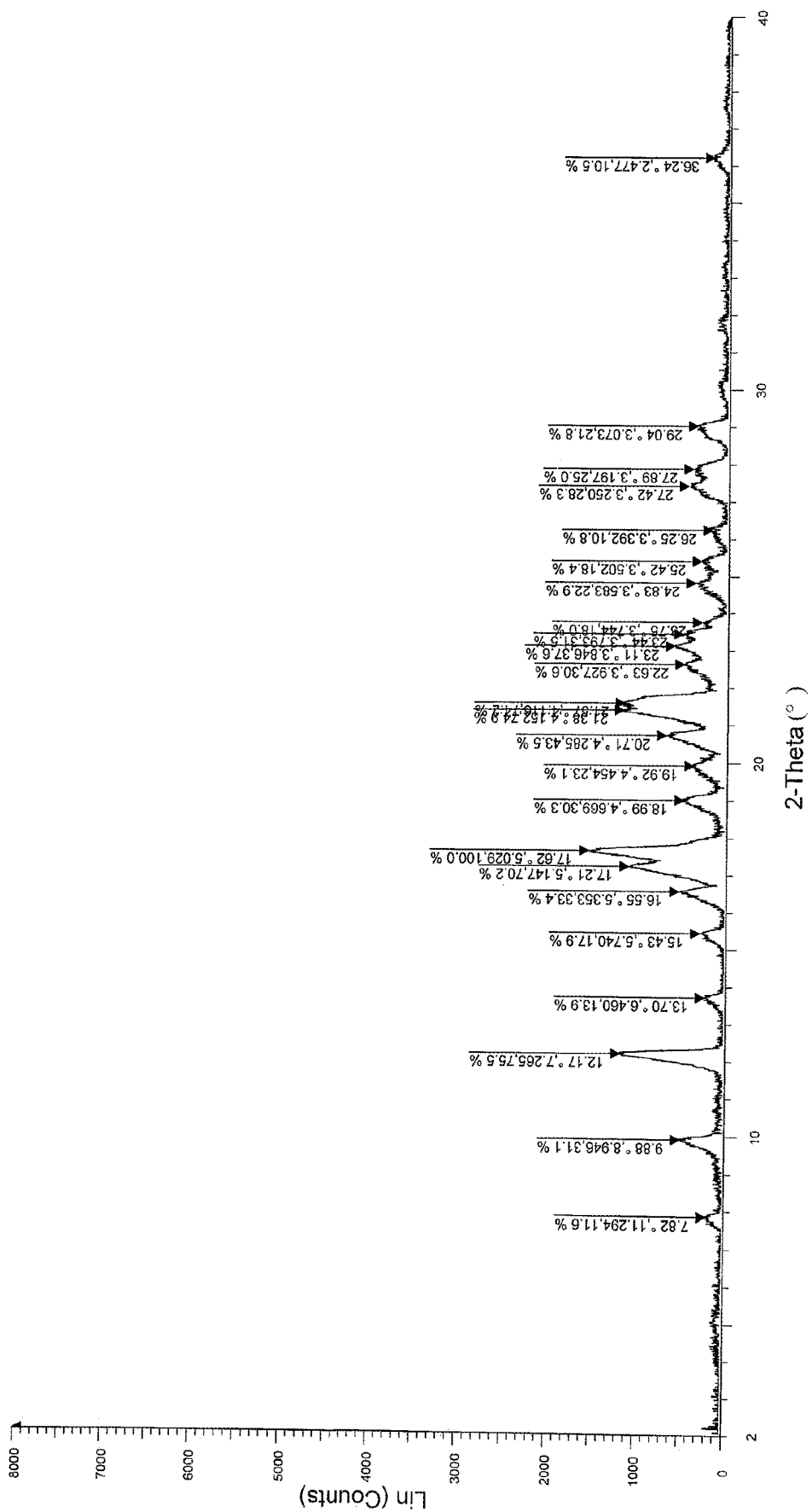
FIG. 2: X-ray diffraction spectrum of the physical mixture of the API compound A and the carrier hydroxypropyl methylcellulose acetate succinate.
Figure 3:
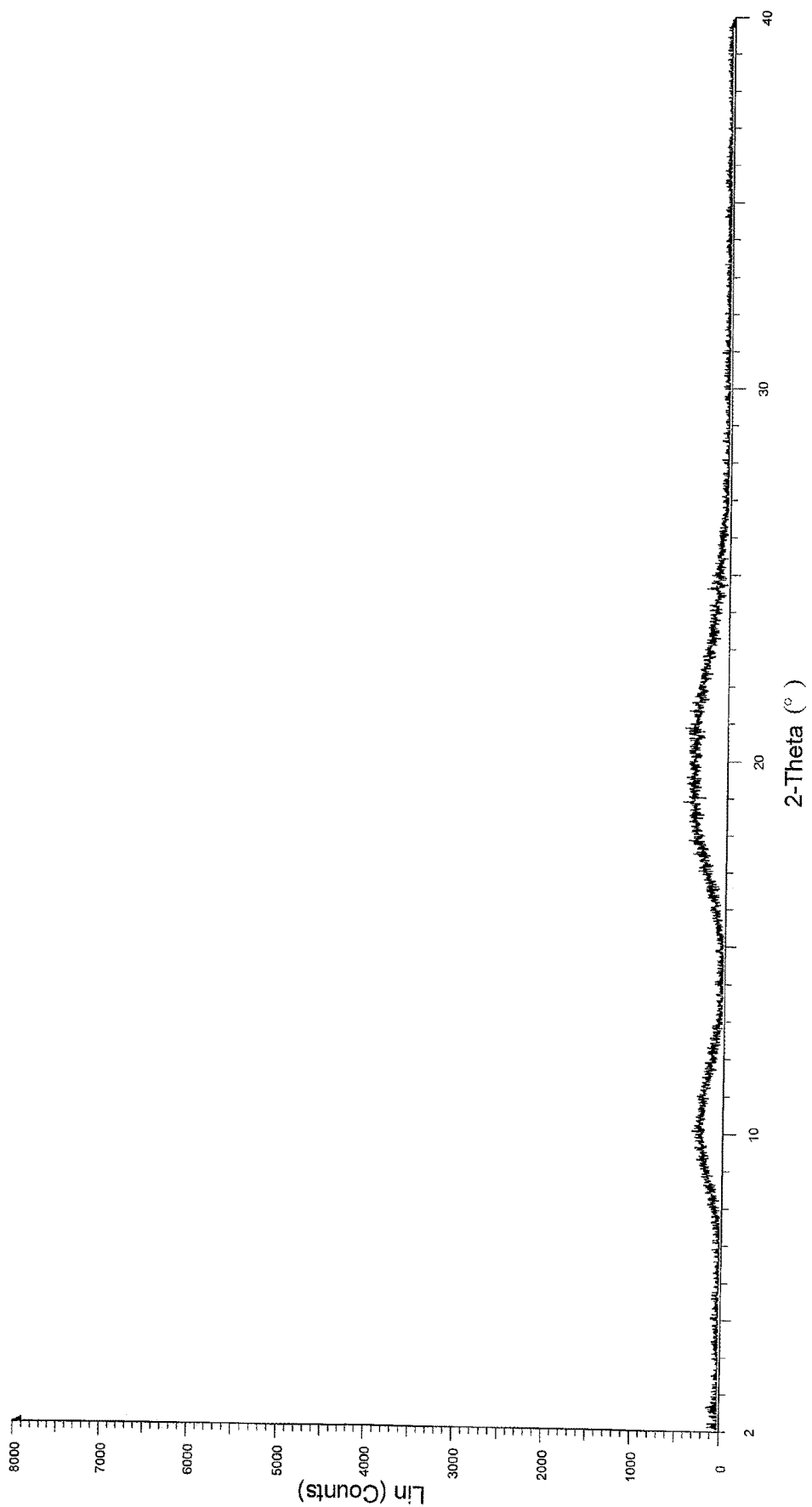
FIG. 3: X-ray diffraction spectrum of the carrier hydroxypropyl methylcellulose acetate succinate.

The present disclosure will be further described in detail with reference to the following examples and experimental examples. These examples and experimental examples are for illustrative purposes only, and should not be considered as limiting the scope of the present disclosure.

Example 1

Preparation of Solid Dispersions

Solid dispersions were prepared with (R)-4-amino-1-(1-(but-2-ynoyl)pyrrolidin-3-yl)-3-(4-(2,6-difluorophenoxy) phenyl)-1,6-dihydro-7H-pyrrolo[2,3-d]pyridazin-7-one (referred to as compound A) and different kinds of carrier materials. Specific formulations are shown in Table 1:

TABLE 1

| Ingredients | Experimental Examples (g) | | |
|---|---|---|---|
| | 1 | 2 | 3 |
| Compound A | 3 | 3 | 3 |
| Hydroxypropyl methylcellulose acetate succinate | — | — | 3 |
| Eudragit L100-55 | — | 3 | — |
| Hydroxypropyl methylcellulose phthalate | 3 | — | — |

Preparation Method (Coprecipitation Method):

Compound A and the carrier material were weighed according to the formulations specified in Table 1, and completely dissolved in N,N-dimethylacetamide (DMF). A prescription amount of purified water was weighed according to the ratio of N,N-dimethylacetamide to purified water of 1:15 (g/g). The solution comprising compound A and the carrier material was added dropwise to the water at a flow rate of 30 g/min, and a white flocculent precipitate was precipitated, filtrated, washed and dried to obtain a solid dispersion.

Dissolution Test

The dissolution rates of the mixtures of API and the carrier of Experimental Examples 1 to 3 were determined according to the second method (paddle method) of the dissolution rate test described in general rule of volume IV of Chinese Pharmacopoeia 2015 Edition. The dissolution test was carried out using 1000 ml of 0.15% aqueous solution of SDS as a dissolution medium at 37±0.5° C., and at a paddle speed of 75 rpm.

TABLE 2

| Time (min) | Dissolution rate (%) | | |
|---|---|---|---|
| | 1 | 2 | 3 |
| 5 | 80.1 | 51.3 | 84.3 |
| 15 | 89.4 | 64.3 | 94.5 |
| 45 | 94.5 | 72.9 | 100.1 |

The results indicated that: when Eudragit L100-55 was used as the carrier material, the dissolution was slow and incomplete, and the dissolution rate was merely about 70% in 45 min, which to some extent will affect the bioavailability of compound A it is formulated into a pharmaceutical drug; when hydroxypropyl methylcellulose phthalate or hydroxypropyl methylcellulose acetate succinate, especially hydroxypropyl methylcellulose acetate succinate was used as the carrier material, the dissolution behavior was significantly improved.

Stability Study

The solid dispersion of Experimental Example 3 was placed at 25° C./60% RH and 40° C./75% RH respectively to investigate the long-term placement stability. Data are shown as follows:

TABLE 3

| Test items | Day 0 | 25° C./60% RH | | | | | | 40° C./75% RH | | | |
|---|---|---|---|---|---|---|---|---|---|---|---|
| | | 3M | 6M | 9M | 12M | 18M | 24M | 1M | 2M | 3M | 6M |
| Total impurity content (%) | 0.22 | 0.22 | 0.23 | 0.23 | 0.23 | 0.28 | 0.28 | 0.22 | 0.22 | 0.22 | 0.23 |
| Crystal form | | Amorphous form | | | | | | Amorphous form | | | |

Example 2

A solid dispersion of Compound A and hydroxypropyl methylcellulose acetate succinate (weight ratio: 1:1) was prepared, which was then pulverized to meet the desired particle size requirement. A prescription amount of the solid dispersion, lactose and microcrystalline cellulose were weighed according to the formulations specified in Table 4, and croscarmellose sodium, crospovidone, sodium carboxymethyl starch or low-substituted hydroxypropyl cellulose were added as the disintegrant, respectively. The mixture was poured into a granulating tank, mixed well, and hydroxypropyl cellulose was added as the binder to prepare granules. The wet and soft material was wet-milled and dried, and then the dry granules (water content less than 3%) were dry-milled. A prescription amount of magnesium stearate was added, and mixed well with the granules. The resulting total mixed granules were compressed into tablets. Specific formulation ratios are shown in Table 4.

TABLE 4

| | Experimental Examples (mg/tablet) | | | |
|---|---|---|---|---|
| Ingredients | 4 | 5 | 6 | 7 |
| Solid dispersion | 200 | 200 | 200 | 200 |
| Lactose monohydrate | 195 | 195 | 195 | 195 |
| Microcrystalline cellulose 101 | 69 | 69 | 69 | 69 |
| Croscarmellose sodium | 25 | — | — | — |
| Crospovidone | — | 25 | — | — |
| Sodium carboxymethyl starch | — | — | 25 | — |
| Low-substituted hydroxypropyl cellulose | — | — | — | 76 |
| Hydroxypropyl methylcellulose E5 | 13 | 13 | 13 | 13 |
| Magnesium stearate | 5.0 | 5.0 | 5.0 | 5.6 |
| Total (mg) | 507 | 507 | 507 | 560 |

Dissolution Test

The dissolution rates of the tablets of Experimental Examples 4 to 7 were determined according to the second method (paddle method) of the dissolution rate test described in general rule of volume IV of Chinese Pharmacopoeia 2015 Edition. The dissolution test was carried out using 1000 ml of 0.15% aqueous solution SDS as a dissolution medium at 37±0.5° C., and at a paddle speed of 50 rpm.

TABLE 5

| | Dissolution rate (%) | | | |
|---|---|---|---|---|
| Time (min) | 4 | 5 | 6 | 7 |
| 5 | 43.2 | 2.8 | 44.8 | 4.1 |
| 15 | 80.5 | 9.2 | 82.6 | 11.2 |
| 45 | 90.0 | 53.6 | 92.5 | 51.5 |

The results indicated that the dissolution of Experimental Examples 5 and 7 was slow, the dissolution rate was merely about 50% in 45 min, and these solid formulations cannot release the pharmaceutically active ingredient rapidly. In contrast, Experimental Examples 1 and 3 exhibited better dissolution characteristics, and the dissolution rate was 90.0% in 45 min.

Example 3

A solid dispersion of Compound A and hydroxypropyl methylcellulose acetate succinate (weight ratio: 1:1) was prepared by a coprecipitation method, which was then pulverized. A prescription amount of the solid dispersion, lactose, microcrystalline cellulose and croscarmellose sodium were weighed according to the formulation specified in Table 6. The mixture was poured into a granulating tank, mixed well, and hydroxypropyl methylcellulose, polyvinylpyrrolidone, pregelatinized starch or hydroxypropyl cellulose, respectively, were added as the binder to prepare granules. The wet and soft material was wet-milled and dried, and then the dry granules (water content less than 3%) were dry-milled. A prescription amount of magnesium stearate was added, and mixed well with the granules. The resulting total mixed granules were compressed into tablets. Specific formulation ratios are shown in Table 6.

TABLE 6

| | Experimental Examples (mg/tablet) | | | | |
|---|---|---|---|---|---|
| Ingredients | 4 | 8 | 9 | 10 | 11 |
| Solid dispersion | 200 | 200 | 200 | 200 | 200 |
| Lactose monohydrate | 195 | 195 | 195 | 195 | 175 |
| Microcrystalline cellulose 101 | 69 | 69 | 69 | 69 | 60 |

TABLE 6-continued

| Ingredients | Experimental Examples (mg/tablet) | | | | |
|---|---|---|---|---|---|
| | 4 | 8 | 9 | 10 | 11 |
| Croscarmellose sodium | 25 | 25 | 25 | 25 | 25 |
| Hydroxypropyl methylcellulose E5 | 13 | — | — | — | — |
| Hydroxypropyl cellulose SSL | — | — | — | 15 | — |
| Pregelatinized starch | — | — | 73.7 | — | — |
| Polyvinylpyrrolidone K30 | — | 22 | — | — | 20 |
| Croscarmellose sodium | — | — | — | — | 15 |
| Magnesium stearate | 5.0 | 5.1 | 5.6 | 5.0 | 5.0 |
| Total (mg) | 507 | 516 | 568 | 509 | 500 |

Dissolution Test

The dissolution rates of the tablets of Experimental Examples 4 and 8 to 11 were determined according to the second method (paddle method) of the dissolution rate test described in general rule of volume IV of Chinese Pharmacopoeia 2015 Edition. The dissolution test was carried out using 1000 ml of 0.15% aqueous solution of SDS as a dissolution medium at 37±0.5° C., and at a paddle speed of 50 rpm.

TABLE 7

| | Dissolution rate (%) | | | | |
|---|---|---|---|---|---|
| Time (min) | 4 | 8 | 9 | 10 | 11 |
| 5 | 43.2 | 45.0 | 34.6 | 57.0 | 53.4 |
| 15 | 80.5 | 70.8 | 59.2 | 82.5 | 78.8 |
| 45 | 90.0 | 93.0 | 85.2 | 93.3 | 95.9 |

The results indicated that the dissolution of Experimental Example 9 was slow and incomplete, and the dissolution rate was merely about 85% in 45 min. In contrast, Experimental Examples 8 to 11 exhibited better dissolution characteristics, and the dissolution rate was 93.0% in 45 min.

Example 4

A solid dispersion of Compound A and hydroxypropyl methylcellulose acetate succinate was prepared by a coprecipitation method, which was then pulverized. A prescription amount of the solid dispersion, lactose, microcrystalline cellulose and croscarmellose sodium were weighed according to the formulation specified in Table 8. The mixture was poured into a granulating tank, mixed well, and polyvinylpyrrolidone was added as the binder to prepare granules. The wet and soft material was wet-milled and dried, and then the dry granules (water content less than 3%) were dry-milled. Extragranular auxiliary materials were added, and mixed well with the granules. The resulting total mixed granules were compressed into tablets. Specific formulation ratios are shown in Table 8.

TABLE 8

| Ingredients | Experimental Examples (mg/tablet) | | | |
|---|---|---|---|---|
| | 12 | 13 | 14 | 15 |
| Compound A | 100 | 100 | 100 | 100 |
| Hydroxypropyl methylcellulose acetate succinate | — | — | 100 | 200 |
| Eudragit L100-55 | 100 | — | — | — |
| Hydroxypropyl methylcellulose phthalate | — | 100 | — | — |
| Lactose monohydrate | 175 | 175 | 175 | 175 |
| Microcrystalline cellulose 101 | 60 | 60 | 60 | 60 |
| Croscarmellose sodium (intragranularly) | 25 | 25 | 25 | 25 |
| Polyvinylpyrrolidone K30 | 20 | 20 | 20 | 20 |
| Croscarmellose sodium (extragranularly) | 15 | 15 | 15 | 15 |
| Magnesium stearate | 5.0 | 5.0 | 5.0 | 5.6 |
| Total (mg) | 500 | 500 | 500 | 600 |

Dissolution Test

The dissolution rates of the tablets of Experimental Examples 12 to 15 were determined according to the second method (paddle method) of the dissolution rate test described in general rule of volume IV of Chinese Pharmacopoeia 2015 Edition. The dissolution test was carried out using 1000 ml of 0.15% aqueous solution of SDS as a dissolution medium at 37±0.5° C., and at a paddle speed of 50 rpm.

TABLE 9

| | Dissolution rate (%) | | | |
|---|---|---|---|---|
| Time (min) | 12 | 13 | 14 | 15 |
| 5 | 40.1 | 55.2 | 60.3 | 63.2 |
| 15 | 50.2 | 67.9 | 80.2 | 82.9 |
| 45 | 65.2 | 85.6 | 97.8 | 98.2 |

The results indicate that: when Eudragit L100-55 was used as the carrier material, the dissolution was slow and incomplete, and the dissolution rate was merely about 65% in 45 min, which will affect the bioavailability of compound A. However, when hydroxypropyl methylcellulose acetate succinate was used as the carrier material, the dissolution rate was significantly improved.

Stability Study

The tablet of Experimental Example 14 was placed at 25° C./60% RH and 40° C./75% RH respectively to investigate the long-term placement stability. Data are shown as follows:

TABLE 10

| Test items | Day 0 | 25° C./60% RH | | | | | 40° C./75% RH | | | |
|---|---|---|---|---|---|---|---|---|---|---|
| | | 3M | 6M | 9M | 12M | 18M | 1M | 2M | 3M | 6M |
| Total impurity content (%) | 0.22 | 0.23 | 0.23 | 0.23 | 0.25 | 0.35 | 0.25 | 0.23 | 0.24 | 0.26 |
| Crystal form | | Amorphous form | | | | | Amorphous form | | | |

Example 5

Pharmacokinetics (PK) Study in Animals 12 beagle dogs were grouped into two groups (6 beagle dogs per group, half male and half female). The beagle dogs were fasted for more than 12 h before the experiment, and food was provided 4 h after the drug administration on the day of the experiment. Water was not deprived during the experiment. The crystal form of compound A and the solid dispersion of compound A, respectively (the ratio of compound A to hydroxypropyl methylcellulose acetate succinate was 1:1, according to the formulation of Experimental Example 3), were administered orally to the two groups of animals with an administration dose of 30 mg/kg. 0.6 mL of blood was taken from climb veins before administration and 0.25, 0.5, 1.0, 2.0, 4.0, 6.0, 8.0, 12, 24 and 72 h after administration. The blood was stored in an ethylenediaminetetraacetic acid (EDTA) anticoagulant tube, and centrifuged for 10 minutes at 3500 rpm (4° C.) to separate the blood plasma. The plasma was stored at −70° C.

The concentration of API in the blood plasma and the administrated solution was determined by liquid chromatography-tandem mass spectrometry (LC/MS/MS). The pharmacokinetic parameters of beagle dogs after drug administration were calculated with the resulting plasma concentration using the non-compartmental model of Phoenix WinNonlin 6.4 software. The results are shown in Table 11.

TABLE 11

| Groups | Dose (mpk) | $C_{max}$ (ng/ml) | $AUC_{0-\infty}$ (ng/ml * h) | $t_{1/2}$(h) | F(%) |
|---|---|---|---|---|---|
| Crystal form of compound A | 30 | 630 ± 530 | 3866 ± 3167 | 3.02 ± 0.65 | / |
| Solid dispersion of Experimental Example 3 | 30 | 4105 ± 1560 | 28247 ± 8060 | 2.67 ± 0.17 | / |

It can be seen from the results in Table 11 that, after compound A was prepared as a solid dispersion, the in vivo absorption of the API was significantly better than that of the crystal form of compound A, indicating that the solid dispersion prepared with hydroxypropyl methylcellulose acetate succinate can significantly increase the bioavailability of compound A after be prepared into a drug and the in vivo absorption of the API.

What is claimed is:

1. A solid dispersion comprising an active ingredient (R)-4-amino-1-(1-(but-2-ynoyl)pyrrolidin-3-yl)-3-(4-(2,6-difluorophenoxy)phenyl)-1,6-dihydro-7H-pyrrolo[2,3-d]pyridazin-7-one or a pharmaceutically acceptable salt thereof and a carrier material, wherein the carrier material is selected from the group consisting of hydroxypropyl methylcellulose acetate succinate and hydroxypropyl methylcellulose phthalate.

2. The solid dispersion according to claim 1, wherein the weight ratio of the carrier material to the active ingredient is not less than 0.5:1.

3. The solid dispersion according to claim 1, wherein the weight ratio of the carrier material to the active ingredient is 0.5:1 to 4:1.

4. The solid dispersion according to claim 1, wherein the solid dispersion consists of the active ingredient (R)-4-amino-1-(1-(but-2-ynoyl)pyrrolidin-3-yl)-3-(4-(2,6-difluorophenoxy)phenyl)-1,6-dihydro-7H-pyrrolo[2,3-d]pyridazin-7-one or a pharmaceutically acceptable salt thereof and the carrier material.

5. A method for preparing the solid dispersion according to claim 1, the method comprising the steps of dissolving the carrier material and the active ingredient or a pharmaceutically acceptable salt thereof together in an organic solvent, removing the organic solvent to obtain the solid dispersion.

6. The method according to claim 5, wherein the organic solvent is removed by a solvent-precipitating method.

7. A solid formulation selected from the group consisting of a tablet, pill, granule and capsule, wherein the solid formation comprises the solid dispersion according to claim 1.

8. The solid formulation according to claim 7, wherein the solid formulation further comprises at least one pharmaceutically acceptable excipient selected from the group consisting of a disintegrant, filler, binder and lubricant.

9. The solid formulation according to claim 8, wherein the solid formulation comprises:

1) 10 mg to 500 mg of the active ingredient or a pharmaceutically acceptable salt thereof;
2) 5 to 15% by weight of a disintegrant;
3) 30 to 90% by weight of a filler;
4) 0.5 to 10% by weight of a binder; and
5) 0.1 to 5% by weight of a lubricant.

10. The solid formulation according to claim 7, wherein when in a medium of 0.15% aqueous solution of sodium dodecyl sulfate (SDS), the dissolution rate (%) of the active ingredient in the solid formulation is 85% or more in 45 min.

11. A method for preparing the solid dispersion according to claim 1, the method comprising suspending and dispersing the carrier material in an organic solvent of the active ingredient or a pharmaceutically acceptable salt thereof, and removing the organic solvent to obtain the solid dispersion.

12. The method according to claim 11, wherein the organic solvent is removed by a solvent-precipitating method.

13. The solid dispersion according to claim 1, wherein the carrier material is hydroxypropyl methylcellulose acetate succinate.

14. The solid dispersion according to claim 1, wherein the weight ratio of the carrier material to the active ingredient is 0.8:1 to 3:1.

15. The solid dispersion according to claim 1, wherein the weight ratio of the carrier material to the active ingredient is 1:1 to 2:1.

16. The solid formulation according to claim 7, wherein when in a medium of 0.15% aqueous solution of sodium dodecyl sulfate (SDS), the dissolution rate (%) of the active ingredient in the solid formulation is 90% or more in 45 min.

\* \* \* \* \*